United States Patent
Dondi et al.

(10) Patent No.: US 6,342,366 B1
(45) Date of Patent: Jan. 29, 2002

(54) LACTOBACILLI STRAINS HAVING INHIBITORY AND/OR MICROBICIDAL ACTIVITY AGAINST PATHOGENIC MICROORGANISMS AND A METHOD FOR INDUCING AND KEEPING SAID ACTIVITY IN LACTOBACILLI CULTURES

(75) Inventors: Giancarla Dondi; Lorenzo Morelli, both of Novara (IT)

(73) Assignee: Proge Farm S.r.L., Novara (IT)

( * ) Notice: Subject to any disclaimer, the term of this patent is extended or adjusted under 35 U.S.C. 154(b) by 0 days.

(21) Appl. No.: 09/285,615

(22) Filed: Apr. 3, 1999

Related U.S. Application Data

(63) Continuation of application No. 08/907,317, filed on Aug. 6, 1997, now abandoned.

(30) Foreign Application Priority Data

Apr. 10, 1998 (IT) .......................................... MI98A0775

(51) Int. Cl.⁷ .............................. C12Q 1/18; C12N 1/20; A01N 63/00
(52) U.S. Cl. ...................... 435/32; 435/252.9; 435/853; 424/93.45
(58) Field of Search ................... 424/93.45; 435/252.9, 435/32, 853

(56) References Cited

U.S. PATENT DOCUMENTS 5,531,988 A * 7/1996 Paul ........................... 424/934

FOREIGN PATENT DOCUMENTS

| DE | 1 208 599 | * 10/1970 |
| EP | 0 353 581 | * 2/1990 |

OTHER PUBLICATIONS

Mital et al. Critical Reviews in Microbiology. 1995. 21 (3) : 175–214.*

Barefoot et al. Applied and Evironmental Microbiology. Oct. 1994. vol. 60, No. 10, pp. 3522–3528.*

Tahara et al. FEMS Microbiology Letters. 1997. 147:287–290.*

In: Bacteriocins of Lactic Acid Bactera. Edited by Dallas G. Hoover et al. Academic Press, Inc. (1993(, pp. 80,81, 153–155, 226–229.*

Luc De Vuyst et al. Microbiology. 1996. 142:817–827.*

* cited by examiner

*Primary Examiner*—Irene Marx
*Assistant Examiner*—Vera Afremova
(74) *Attorney, Agent, or Firm*—Walter H. Schneider

(57) ABSTRACT

A method for the treatment of lactobacilli cultures is disclosed, characterized in that said cultures are added with an aliquot of culture supernatant of pathogenic microorganisms, or with the same pathogenic microorganisms optionally suitably inactivated. In particular, *Lactobacillus gasseri* BCCM LMG P-18137, *Lactobacillus gasseri* BCCM LMG P-17632 and *Lactobacillus crispatus* BCCM LMG P-17631.

1 Claim, No Drawings

LACTOBACILLI STRAINS HAVING INHIBITORY AND/OR MICROBICIDAL ACTIVITY AGAINST PATHOGENIC MICROORGANISMS AND A METHOD FOR INDUCING AND KEEPING SAID ACTIVITY IN LACTOBACILLI CULTURES

This application is a con't of Ser. No. 08/907,317 filed Aug. 6, 1997 abandoned.

FIELD OF THE INVENTION

The present invention relates to lactobacilli able to inhibit the growth of pathogenic microorganisms and/or to exert a microbicidal activity against them (more particularly two novel *Lactobacillus gasseri* strains and one *Lactobacillus crispatus* strain) and a method for inducing and/or enhancing and/or keeping said activity in lactobacilli cultures.

The invention also relates to a culture medium for lactobacilli which can be used in combination with said induction method.

TECHNOLOGICAL BACKGROUND

Lactobacilli are widespread in nature. A number of species are present in alimentary products (milk, yogurt, fruits, vegetables and the like), whereas only some strains are usual eubiotic saprophytes of the intestinal and/or urogenital flora.

In most cases known lactobacilli, when administered through the oral or vaginal or any other routes, restore the physiological bacterial flora, but are per se not able of inhibiting the growth of pathogens or of exerting any microbicidal activity against them.

Only some bacterial strains have recognizedly developed this natural capability of inhibiting the growth of pathogenic microorganisms when placed in the same culture.

In fact, EP 0 353 581 reports that a *Lactobacillus fermentum* strain, deposited at the CNCM of the Institut Pasteur, recovered from human vagina, is capable of counteracting in vitro the growth of *Candida albicans*.

Furthermore some other lactobacilli, in particular a *Lactobacillus paracasei* strain recovered from human intestine (Italian Pat. Appl. N° MI97A000426 filed on Feb. 27, 1997), have been found to have, in addition to the other features cited in the above mentioned Patent Application, the capability of causing in vitro an inhibition area when seeded in agarized Petri dishes in which *Candida albicans* had concomitantly been grown.

As a whole, these findings prove that the activity of lactobacilli, recovered from various human habitats, against pathogens, occurs naturally.

Moreover, such an antimicrobial activity is known to be related to the ability of some lactobacilli to physiologically produce bacteriocins and/or other similar substances, said production of bacteriocins being sometimes related to the presence of plasmids.

The stabilization of an industrially important phenotypic character in lactobacilli by addition of specific substances has been described in GB 1 560 208, wherein the capability of producing lactic acid was induced in lactobacilli.

It has now been found that only some lactobacilli, recovered from human physiological habitats, when seeded in Petri dishes containing agarized medium in which some pathogens had previously been seeded and grown, exert an inhibitory or microbicidal action against such pathogens.

These properties are related to the ability of some lactobacilli to physiologically produce bacteriocins and/or, other similar substances, having bactericidal or microbicidal action. However, such bacterial strains having these characteristics can effectively be used in therapy only if they keep and/or increase said properties in time. It is moreover desirable to induce the inhibitory activity against pathogens in lactobacilli strains which are not per se capable of exerting said activity.

The ability of lactobacilli to produce bacteriocins and/or, other similar substances, is affected by a number of technical factors such as the composition of the culture medium and the incubation conditions (Temperature, pH, Oxygen).

Moreover, any antimicrobial substances produced are generally detected in laboratory conditions which are quite different from the original ones and in which the specific genetic determinants are usually constitutively expressed. Inducible genes are hardly detected by the usual laboratory assays.

DISCLOSURE OF THE INVENTION

The present invention relates to a method for producing lactobacilli strains having microbicidal activity useful for the therapeutic and/or prophylactic treatment of pathologies of the gastrointestinal and/or urogenital systems in humans.

The method further provides for maintaining or increasing the ability to produce antimicrobial substances in those lactobacilli strains which already have these properties, and even to induce and detect the said ability in those lactobacilli which, although having such an ability, cannot exert it.

Preferably, the lactobacilli strains subject to this treatment derive from the physiological intestinal and/or vaginal bacterial flora of a healthy human, and are typically obtained from biological samples containing a multiplicity of bacterial species, isolated by conventional techniques.

Before being treated according to the process of the invention, said samples are usually subjected to suitable pre-treatments according to conventional methods in order to maintain the strains until use.

It is an object of the present invention to provide a method for stimulating the cultures, traditionally prepared as described above, to produce specific antimicrobial substances.

The lactobacilli strains to be treated are contacted with the pathogenic strain against which the antimicrobial action has to be induced, or with its supernatant (where supernatant means the liquid, sterilised and stored in refrigerator or in freezer until use, which separates from the cell pellet upon centrifugation of a pathogenic culture which is obtained growing a strain of the appropriate pathogen in a suitable culture medium and under suitable growth conditions).

Alternatively, the culture medium for lactobacilli can also be contacted with cells of pathogenic microorganisms inactivated by chemical or physical treatments.

After that the, lactobacilli and pathogenic strain or its supernatant are seeded and grown simultaneously in the suitable culture medium. This step of incubation of the strains is typically carried out on a plate, in a nutritive medium added with agar, preferably on MRS agarized medium.

The resulting lactobacilli strains are then centrifuged and resuspended in a medium containing the specific excipients, then frozen so as to keep the strain viable.

The present invention further relates to lactobacilli strains and the bacterial cultures obtained according to the process of this invention, and to compositions comprising pharmaceutical, dietary or alimentary formulations containing the lactobacilli as the principal active ingredient together with a pharmaceutically or physiologically acceptable carrier.

The process of the invention provides lactobacilli strains able to inhibit different pathogens and/or exert a microbicidal action against them, suitable for formulation in pharmaceutical preparations, which proved to be extremely effective and advantageous in the treatment of pathologies related to the presence of pathogenic agents sensitive to some lactobacilli strains.

According to a preferred embodiment of the present invention, the bacterial strains to be treated are derived from the physiological saprophytic flora of healthy subjects.

In order to activate the inducible genes of lactobacilli to produce antimicrobial substances, the bacterial cultures are contacted with cultures of pathogenic strains such as Candida sp., Proteus sp., *Escherichia coli, Trichomonas vaginalis, Streptcoccus* β-*haemolyticus,* Enterococcus sp, or with the supernatants thereof.

"Supernatant" means the culture medium (for example LB broth for *Escherichia coli,* or Malt Broth for Candida sp.) in which a culture of the pathogenic strain has been grown in the suitable growth conditions (for example 18 hours in aerobic conditions at 37° C. for *Escherichia coli,* and 24 hours in aerobic conditions at 30° C. for Candida). At the end of the growth period described above, the culture is centrifuged and the liquid separated from the cell pellet is withdrawn. This liquid is then sterilised (for example by filtration through cellulose filters with porosity not higher than 0.45 micron) and stored in refrigerator or freezer until use.

Alternatively to the addition of cultures of pathogens or of supernatants thereof, the lactobacilli culture medium can also be added with cells of pathogenic microorganisms inactivated by chemical (chloroform, formaldehyde) or physical (heat or radiations) treatments.

According to a preferred embodiment of the invention, the lactobacilli strain to be treated is grown, at the same time as the pathogenic strain, in a lactobacilli medium, preferably MRS medium (de Man J. C., Rogosa, M. and M. E. Sharpe, Journal of Applied Bacteriology, 23, 130–135, 1960) the composition of which is reported in the subsequent table.

TABLE

| composition of MRS medium (pH = 6.2–6.4) | |
|---|---|
| meat extract | 8 g |
| yeast extract | 4 g |
| proteoso peptone | 10 g |
| sodium acetate | 5 g |
| dibasic ammonium acetate | 2 g |
| dibasic potassium phosphate | 2 g |
| glucose | 20 g |
| saline solution A | 5 ml |
| tween 80 | 1 ml |
| bidistilled water | 1000 ml |

Subsequently, the strains inoculated in the test-tubes tubes containing the MRS medium described above are incubated in thermo-stat at +37° C., in anaerobiosis conditions.

The lactobacilli strains are grown in these optimum growth conditions for 24 hours in liquid MRS, then they are centrifuged and resuspended, preferably in 0.5 ml of liquid MRS, containing a varying concentration of glycerol, preferably ranging from 20 to 50%. This procedure keeps the treated strain viable.

Laboratory assays prove that the addition of either supernatant liquid, as defined above, in a 0.01% to 5.00% V/V ratio, or of the pathogenic strain to the lactobacilli culture medium, increases the production of inhibiting substances.

The following examples further illustrate the invention.

EXAMPLE 1

About 100 mg of a selected freeze-dried lactobacilli strain of about $10^{10}$ UFC/g were grown at 37° C. overnight in 10 ml of MRS broth. 100 µl of the above suspension were then placed in 9.9 ml of MRS broth and incubated for 5 h at 37° C.

The same lactobacilli strain was previously treated, according to the procedure of the invention, growing it in the presence of Candida supernatant.

A sample of pathogen (Candida) was prepared from a slant culture and grown overnight at 37° C. in about 50 ml of Sabouraud.

1 ml of *Candida albicans* (1 McF) was seeded on agarized Petri dishes and dried. Each dish was then seeded with about 30 µl of the different lactobacilli samples. The dish was incubated at 37° C. for 24 h in anaerobiosis and for 24 h in aerobiosis.

Inhibition areas were observed where the untreated lactobacilli sample had been seeded, and an increase in said areas was also evidenced in the plates seeded with the lactobacilli sample treated according to the procedure of the invention.

EXAMPLE 2

A test to assay the specific activity of a selected lactobacilli strain against *Streptococcus* β-*haemolyticus* was carried out, using the medium Bacto-Lactobacillus-MRS-Broth MRS-Broth (Difco code 0881) solidified by addition of 2% of agar. Said medium, after sterilization in autoclave, was distributes in Petri dishes in a ratio of 20 ml per dish and left to solidify.

The inoculum for each test consisted of suitable dilutions of a suspension of the tested strain of turbidity 1 McF.

An amount of 0.1 ml of the inoculum suspension was uniformly spread on the surface of the agarized MRS medium distributed as above; subsequently a smear of each lactobacilli strain to be tested was carried out; finally the thus prepared dishes were incubated at a temperature of 37° C. for 48 hours before reading the results.

The antagonistic activity was considered only in the presence of an evident inhibition area in the growth of the Streptococcus strain around the smear of the tested Lactobacillus.

The results proved that the antagonistic activity shown by the reference strain is markedly lower than that of the same strain previously treated according to the procedure of the invention.

Lactobacilli strains, and in particular 2 strains of *Lactobacillus gasseri* and 1 strain of *Lactobacillus crispatus,* were found to already exert physiologically an inhibitory activity against pathogenic agents such as *Candida albicans* and *Streptococcus* β-*haemolyticus.*

Said strains are a further object of the invention and were deposited according to Budapest Treaty at the Belgian Coordinated Collection of Microorganisms—BCCM LMG Collection Universiteit Gent, K. L. Ledeganckstraat 35, B-9000 Gent, Belgium under the following accession numbers:

*L. gasseri,* isolated from human intestine: LMG-P-17632, 29.11.1996;

*L. gasseri*, isolated from human vagina: LMG-P-18137, 26.09.1997;

*L. crispatus*, isolated from human vagina: LMG-P-17631, 29.11.1996;

The taxonomic characterization was carried out using conventional methods such as fermentation tests of hydrocarbons (API 50 CHL$^{(R)}$, Biomerieux), analysis of cell morphology, Gram reactions, oxidase and catalase reactions, SDS-PAGE analysis and "Cluster analysis".

Some characteristics of the strains of the invention are reported below.

*Lactobacillus gasseri* P-18137

Cell morphology: single, double, chained, immobile, asporogenic rods;
Gram coloration: positive;
Oxidase reaction: negative;
Catalase reaction: negative;
Fermentation of sugars positive for: Galactose, D-glucose, D-fructose, Mannitol (+/−), Maltose, Saccharose, Threalose, Melezitose, Starch, Glycogen, D-Tagatose.

*Lactobacillus gasseri* P-17632

Cell morphology: chained, immobile, asporogenic rods;
Gram coloration: positive;
Oxidase reaction: negative;
catalase reaction: negative;
Fermentation of sugars positive for: Galactose, D-glucose, D-fructose, D-Mannose, Arbutin, Salicin (+/−), Cellobiose, Maltose, Lactose, Saccharose, Threalose, Starch (+/−), b-Gentiobiose (+/−), D-Turanose, D-Tagatose (+/−).

*Lactobacillus crispatus* P-17631

Cell morphology: single, double, immobile, asporogenic rods;
Gram coloration: positive;
Oxidase reaction: negative;
Catalase reaction: negative;
Fermentation of sugars positive for: Galactose, D-glucose, D-fructose, Mannitol (+/−), Maltose, Saccharose, Threalose, Melezitose, Starch, Glycogen, D-Tagatose.

The strain of vaginal *L. gasseri* P-18137 was found to be active in inhibiting the growth of *Streptococcus β-haemolyticus* group B strains clinically isolated in a statistically significant way, with marked inhibition areas ranging from 2 to 10 mm on Bacto-Lactobacillus MRS-Broth medium (DIFCO 0881=2% of agar).

On the other hand, the strain of intestinal *L. gasseri* P-17632, proved to be active in inhibiting the growth of Candida DSM 70163 and 2361 strains, in MRS medium with inhibition areas ranging from 2 to 8 mm.

The vaginal strain of *L. crispatus* P-17631 proved to be active in inhibiting the growth of Candida strains in MRS medium with varying inhibition areas.

The results obtained in vitro can be reproduced in vivo administering freeze-dried cultures of the said lactobacilli, obtained according to the method of the present invention, directly as they are or suitably formulated in pharmaceutical, dietary or alimentary formulations.

Depending on the habitat from which the various strains have been isolated, they can optionally be included in formulations intended for, but not limited to, such an habitat.

The lactobacilli according to the present invention can be administered as they are, or added with a pharmaceutically or anyway physiologically acceptable carrier, to obtain various kinds of formulations, such as pharmaceutical compositions, dietary supplements or alimentary products, which are further objects of the present invention.

Thus, for example, the claimed vaginal strains can also, but not only, be administered as gynaecological formulations (such as vaginal capsules, vaginal tablets, washes, etc.).

The present preparations or formulations contain at least one lactobacilli strain according to the invention, preferably mixtures of at least one lactobacilli strain of the invention, in particular in an amount effective for the intended therapeutical, prophylactic or probiotic treatments, and they can be prepared according to conventional techniques.

The carrier can contain excipients, additives, diluents or other useful substances, provided they are pharmacologically or physiologically acceptable.

The claimed lactobacilli strains, when administered in the form of the above mentioned formulations, are useful for the topical treatment of pathologies deriving from abnormal proliferation of the pathogenic agents which are sensitive to said strains.

What is claimed is:

1. A method of enhancing the inherent antimicrobial activity of a biologically pure culture of a strain of Lactobacillus towards a target pathogenic microorganism, wherein the Lactobacillus strain has all of the identifying characteristics of a strain selected from the group consisting of *Lactobacillus gasseri* BCCM LMG P-18137, *Lactobacillus gasseri* BCCM LMG P-17632 and *Lactobacillus crispatus* BCCM LMG P-17631, and the target pathogenic microorganism is selected from the group consisting of Candida, β-hemolytic Streptococcus, Proteus, Escherichia and Trichomonas, which comprises adding to the liquid culture medium of a biologically pure culture of said Lactobacillus strain, a composition consisting of supernatant from the culture of said target pathogenic microorganism, wherein said supernatant is added at a ratio of 0.01 to 5.00% v/v prior to cultivation of the Lactobacillus strain in said liquid culture medium.

* * * * *